US010203316B2

(12) United States Patent
MacFarland et al.

(10) Patent No.: US 10,203,316 B2
(45) Date of Patent: Feb. 12, 2019

(54) COLORIMETRIC DETERMINATION OF AQUEOUS NITRATE CONCENTRATION

(71) Applicant: Hach Company, Loveland, CO (US)

(72) Inventors: Darren Kent MacFarland, Windsor, CO (US); Brendan Easley Young, Fort Collins, CO (US)

(73) Assignee: HACH COMPANY, Loveland, CO (US)

(*) Notice: Subject to any disclaimer, the term of this patent is extended or adjusted under 35 U.S.C. 154(b) by 151 days.

(21) Appl. No.: 15/223,781

(22) Filed: Jul. 29, 2016

(65) Prior Publication Data

US 2018/0031535 A1  Feb. 1, 2018

(51) Int. Cl.
*G01N 31/22* (2006.01)
*G01N 33/18* (2006.01)
*G01N 21/78* (2006.01)
*B01J 31/24* (2006.01)
*C07C 323/66* (2006.01)
*C07D 311/82* (2006.01)
*B01J 31/18* (2006.01)
*B01J 31/28* (2006.01)
*B01J 31/30* (2006.01)

(52) U.S. Cl.
CPC ........ *G01N 33/182* (2013.01); *B01J 31/1875* (2013.01); *B01J 31/28* (2013.01); *B01J 31/30* (2013.01); *C07C 323/66* (2013.01); *C07D 311/82* (2013.01); *G01N 21/78* (2013.01); *G01N 31/227* (2013.01); *B01J 31/2404* (2013.01); *B01J 2231/70* (2013.01); *B01J 2531/64* (2013.01); *B01J 2540/32* (2013.01); *C07C 2603/50* (2017.05); *Y10T 436/173076* (2015.01)

(58) Field of Classification Search
CPC . B01J 2531/64; B01J 31/2409; C07D 311/82; G01N 21/78; G01N 31/227; G01N 33/18; G01N 33/182; Y10T 436/17; Y10T 436/173076; Y10T 436/18
USPC ..... 436/106, 110, 119, 164, 166; 422/82.05, 422/82.09
See application file for complete search history.

(56) References Cited

U.S. PATENT DOCUMENTS

| 4,424,277 A * | 1/1984 | Bodart ............... G01N 31/227 436/110 |
| 4,690,902 A * | 9/1987 | Bitsch ................ G01N 31/227 422/423 |
| 5,236,848 A * | 8/1993 | Bitsch ................ G01N 21/293 436/110 |
| 9,052,292 B2 * | 6/2015 | Rudde ................ G01N 31/227 |
| 2018/0031536 A1 * | 2/2018 | MacFarland ......... G01N 33/188 |

OTHER PUBLICATIONS

Marom et al. Organic Letters, vol. 13, No. 20, pp. 5532-5535, Sep. 29, 2011.*
Marom et al. Journal of Organic Chemistry, vol. 76, pp. 5240-5246, May 25, 2011.*

* cited by examiner

*Primary Examiner* — Maureen Wallenhorst
(74) *Attorney, Agent, or Firm* — Ference & Associates LLC

(57) ABSTRACT

A method of measuring nitrate concentration in an aqueous sample include mixing the aqueous sample with a water-soluble thioether compound including a chromophore group in the presence of a water soluble catalyst; measuring a color change, and correlating the color change to nitrate concentration.

14 Claims, 13 Drawing Sheets

1) $CH_2Cl_2$, RT
2) MeI/NEt$_3$
3) BF$_3$;Et$_2$O
4) Na-(PEG)-CH$_3$

BODIPY-derived thiomethyl ether

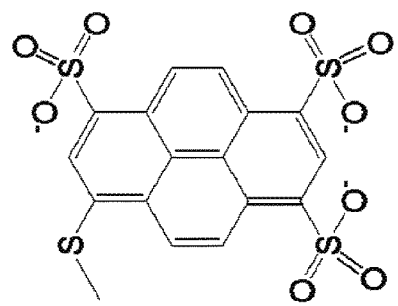
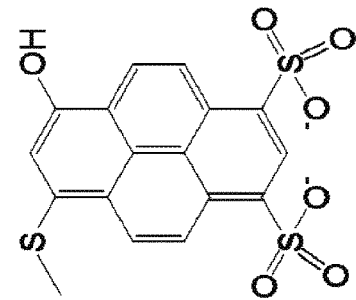
1) Tf₂O
2) Pd(PPh₃)₄, NaSCH₃
1) Tf₂O (1 eq)
2) Pd(PPh₃)₄, NaSCH₃
Fig. 6G
Fig. 6H
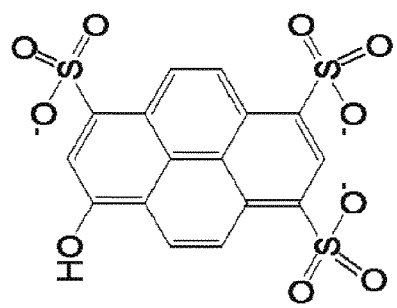
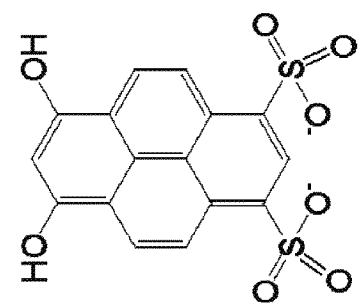

COLORIMETRIC DETERMINATION OF AQUEOUS NITRATE CONCENTRATION

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Determination of aqueous nitrate concentration is important for a variety of public and commercial applications. Nitrate is a common contaminate in water, and high quantities of nitrates in drinking water can be harmful to people and animals. Thus, there is a need to carefully monitor nitrate levels in water. Limits on acceptable nitrate concentration have been established for drinking water. Nitrate concentrations may, for example, be monitored in drinking water supplies, sewage, waste water, water remediation, biological samples, sea water, etc.

Methodologies for measuring aqueous nitrate concentration include spectrophotometry, colorimetry, chromatography, ion selective electrodes, etc. Various shortcomings exist with these methods including toxicity of reagents, cost, sensitivity, selectivity, variability, range, stability, time requirements, portability, etc.

In a number of colorimetric nitrate tests, nitrate is first reduced to nitrite, followed by nitrite analysis. Typically, reduction of nitrate to nitrite is accomplished using cadmium. Then, nitrite concentration is determined using the Griess assay or test. Nitrate concentration is directly related to nitrite concentration. However, cadmium may be toxic and is likely to be prohibited for use in water testing. Moreover, shaking is required in such systems, which may affect the surface reaction that occurs in the use of cadmium to reduce nitrate to nitrite, resulting in variability in testing. Zinc has also been used as a reductant in the nitrate test, but Zn is not as selective as Cd and can result in over-reduction of the nitrate to NO.

Portable water testing equipment such as the Portable Parallel Analyzer™ (available from Hach Company of Loveland, Colo.) have been developed in which the test reagents are deposited (dried) upon a test element (for example, the CHEMKEY® test element available from Hach Company) that can be easily inserted into the equipment and utilized in field testing. The nature of the test elements and associated equipment limit or prevent the use of solid reagents. In that regard, water soluble reagents of an analysis system are dried on a test element. Insoluble solids are difficult to deposit on test elements/chips. Solid reagents in nitrate testing, such as cadmium and zinc, cannot be used in such testing equipment.

The sulfoxidation of thioethers with nitrate as the oxidant and a homogeneous Mo/Cu(II) co-catalyst system has been reported as a pathway to sulfoxides in organic solvent such as acetonitrile. A variety of thioethers were shown to undergo the reaction to a greater or lesser extent. Organic-soluble thioether reagents and catalysts were also shown to be suitable for detection of nitrates in certain environments.

SUMMARY

A method of measuring nitrate concentration in an aqueous sample include mixing the aqueous sample with a water-soluble thioether compound including a chromophore group in the presence of a water soluble catalyst; measuring a color change, and correlating the color change to nitrate concentration. The water-soluble thioether compound may be chosen to oxidize in the presence of nitrate. The water-soluble thioether compound may, for example, have the formula:

wherein $R^3$ is a hydrophilic chromophore group and $R^2$ is a $C_1$-$C_6$ alkyl group or a polyalkyleneoxide group. The polyalkyleneoxide (for example, polyethylene glycol or PEG) may, for example, include 4 to 5000 carbon atoms.

The hydrophilic chromophore group may, for example, include or be a residue of a water-soluble conjugated chromophore. The hydrophilic chromophore group may, for example, include or be residue of a water-soluble, substituted aromatic chromophore.

In a number of embodiments, the hydrophilic chromophore is selected from the group consisting of a hydrophilic diarylmethane chromophore, a hydrophilic triarylmethane chromophore, a hydrophilic xanthene chromophore, a hydrophilic boron-dipyrromethene chromophore and a hydrophilic pyrene chromophore. The initial color wavelength of the hydrophilic chromophore group may, for example, be between 500 and 700 nm in a number of representative examples.

The water soluble catalyst may include a catalyst having the formula $MoO_2Cl_2(L)_2$ wherein L is a hydrophilic group. L may, for example, be or include a water soluble phosphine group. In a number of embodiments, L is trisulfonatedtriphenylphosphineoxide. In a number of embodiments, the water soluble catalyst (or catalyst system) further includes a cocatalyst such as a $Cu^{2+}$ co-catalyst.

The color change may, for example, occur in the visible light spectrum. In a number of embodiments, the color change occurs between the wavelengths of 500 and 700 nm. The color change may, for example, be measured using a spectrometer, colorimeter, photometric device, color disc, color block, or the like. In a number of embodiments, the range of nitrate detection is between about 0 and 15 ppmw.

A water-soluble compound had the formula:

wherein $R^3$ is a hydrophilic chromophore group and $R^2$ is a $C_1$-$C_6$ alkyl group or a polyalkyleneoxide group. The polyalkyleneoxide (for example, polyethylene glycol or PEG) may, for example, include 4 to 5000 carbon atoms.

The hydrophilic chromophore group may, for example, include or be a residue of a water-soluble conjugated chromophore. The hydrophilic chromophore group may, for example, include or be residue of a water-soluble, substituted aromatic chromophore.

In a number of embodiments, the hydrophilic chromophore is selected from the group consisting of a hydrophilic diarylmethane chromophore, a hydrophilic triarylmethane chromophore, a hydrophilic xanthene chromophore, a hydrophilic boron-dipyrromethene chromophore and a hydrophilic pyrene chromophore.

A kit or system for measuring aqueous nitrate concentration includes an analysis system including a water-soluble thioether compound including a chromophore group and a water-soluble catalyst, a system to measure a color change, and a system to correlate the color change to nitrate concentration. The water-soluble thioether compound including a chromophore group and the water-soluble catalyst may, for example, be as described above. The system to measure color change may, for example, include a spectrometer, colorimeter, photometric device, color disc, color block, or the like. The system to measure color change and the system to correlate color change may, for example, include or be incorporated within a portable analyzer or portable analyzer system. The analysis system components may, for example, be deposited on or within a test element insertable into a portable analyzer. The analysis system components may, for example, be deposited upon a surface within a test element in an aqueous solution and dried (that is, the water removed therefrom).

A kit for measuring aqueous nitrate concentration includes an analysis system including a water-soluble thioether compound including a chromophore group and a water-soluble catalyst. The analysis system components may, for example, be deposited on or within a test element insertable into a portable analyzer. The analysis system components may, for example, be deposited upon a surface within a test element in an aqueous solution and dried (that is, the water removed therefrom).

An analysis system includes a mixture of a water-soluble thioether compound including a chromophore group and a water-soluble catalyst.

A water-soluble catalyst has the formula $MoO_2Cl_2(L)_2$ wherein L is a hydrophilic group. In a number of embodiments, L is or includes a water soluble phosphine. L may, for example, be trisulfonated-triphenylphosphineoxide.

The present kits, systems, methods and compositions, along with the attributes and attendant advantages thereof, will best be appreciated and understood in view of the following detailed description taken in conjunction with the accompanying drawings.

BRIEF DESCRIPTION OF THE DRAWINGS

FIG. 6G illustrates a representative example of a synthetic scheme for synthesis of a thioether based upon a pyrene derived chromophore.

FIG. 6H illustrates a representative example of a synthetic scheme for synthesis of a thioether based upon another pyrene derived chromophore.

DETAILED DESCRIPTION

Figure 1:
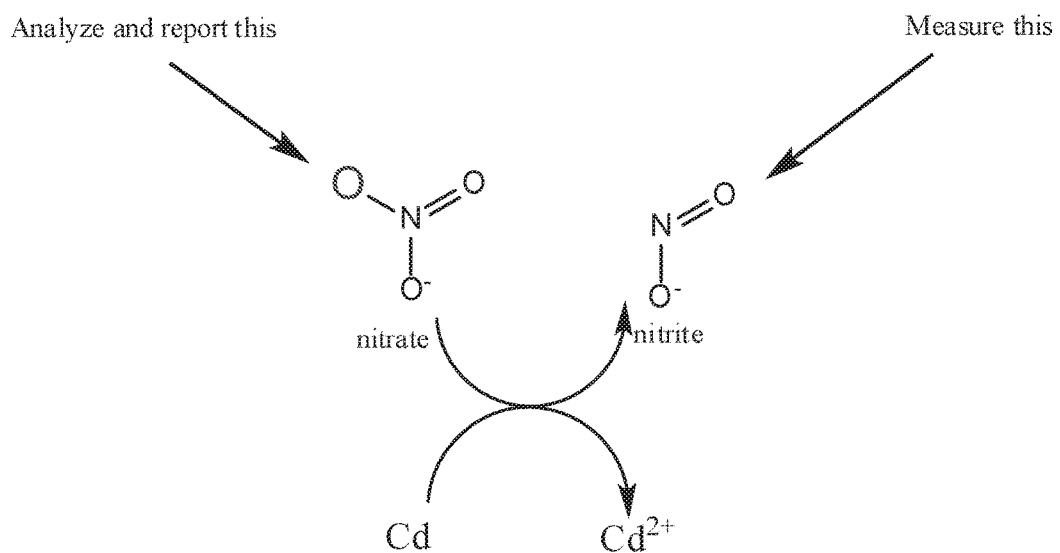
FIG. 1 illustrates reduction of nitrate using cadmium.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a thioether" includes a plurality of such thioethers and equivalents thereof known to those skilled in the art, and so forth, and reference to "the thioether" is a reference to one or more such thioethers and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

In a number of embodiments hereof, water soluble thioether compounds including a covalently attached chromophore group are synthesized. In the presence of nitrate and a water soluble catalyst, the water soluble chromophoric thioether compounds undergo sulfoxidation with a concurrent color change. The color change correlates to nitrate concentration. Further, depending on the extinction coefficient of the particular chromophore species attached, different measurement ranges are provided. In a number of other embodiments, kits for the determination of aqueous nitrate concentration based on the thioether chemistry described above are provided. In a number of embodiments hereof, the water-soluble chromophoric thioether compounds and catalysts hereof are deposited on test elements, stored, and later used with a portable analysis system. Thus, the analysis systems hereof are, for example, readily used with analysis systems such as the Portable Parallel Analyzer (PPA) and corresponding CHEMKEYs test elements of Hach Company.

Advantages of these systems, methods, compositions, and kits for nitrate determination hereof compared to currently available tests include the elimination of toxic metals, the elimination of vigorous shaking to mix solids, the water solubility of all method components, the ability to deposit all test components on a test element to be later used in portable analysis systems, elimination of the Griess assay reagents, the ability to tailor extinction coefficient of the chromophoric complex, the ability to tailor the reactivity/reaction rate of the chromophoric thioether compounds, and the ability to tailor the water-solubility of the chromophoric thioether complex.

As described above, there are several methods for the determination of aqueous nitrate concentration. The colorimetric method is widely used as a result of its ease and portability.

Figure 2:
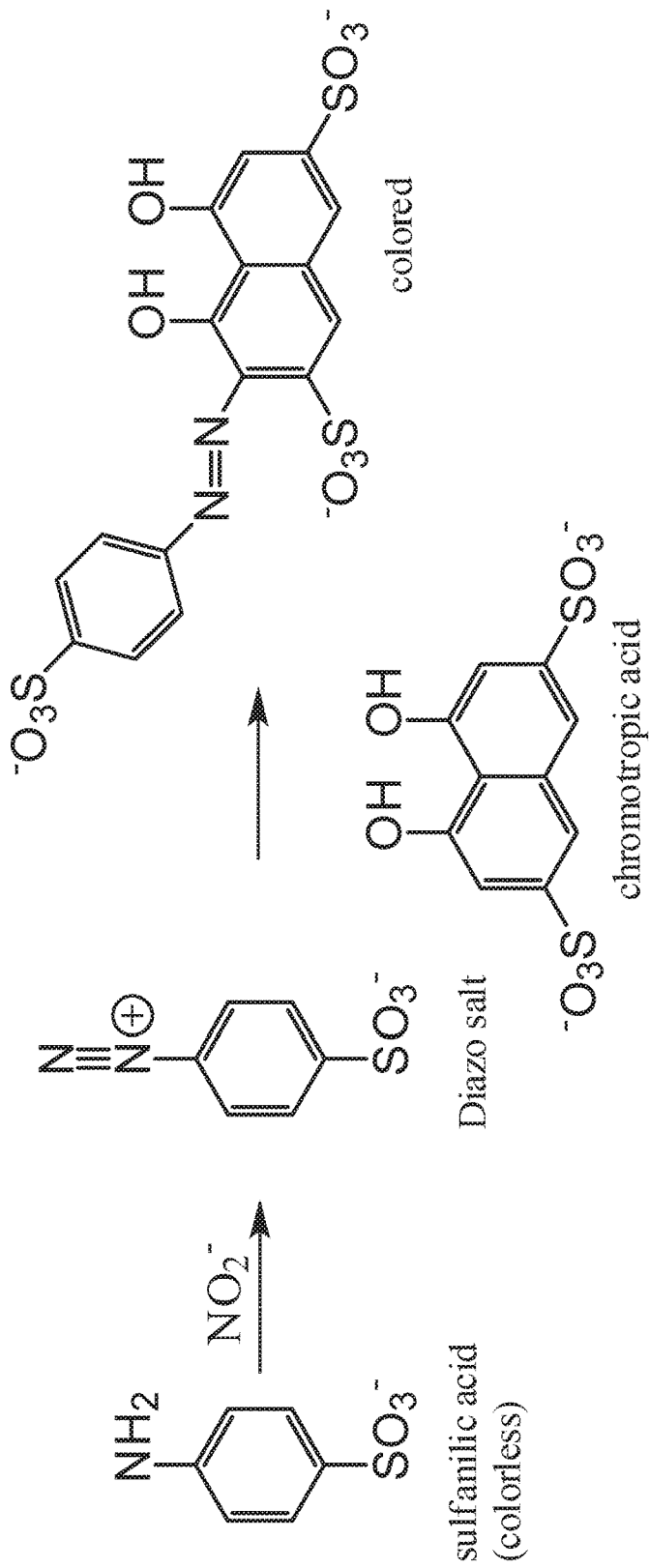
FIG. 2 illustrates a representative example of a Griess assay and reagent system.

In many colorimetric nitrate tests, nitrate is first reduced to nitrite, followed by nitrite analysis. Typically, reduction of nitrate to nitrite is accomplished using cadmium or a similar reductant (e.g., zinc). FIG. 1 illustrates reduction of nitrate to nitrite using cadmium metal. Cadmium metal is oxidized to $Cd^{2+}$ while nitrate ($NO_3^{-1}$) is reduced to nitrite ($NO_2^{-1}$). Cd is not a catalyst, it is consumed (i.e., sacrificially) in the reaction. Nitrite concentration may, for example, be determined using the Griess assay, a representative example of which is illustrated in FIG. 2. The Griess assay refers to a class of reagents/reactions that is well known in the nitrate/nitrite detection arts. In the embodiment of the Griess assay illustrated in FIG. 2, nitrite reacts with sulphanilic acid (or another aniline derivative) in acidic solution to form a diazonium salt. The diazonium salt is then reacted with an azo dye agent (e.g., chromotropic acid) to form a colored azo dye. The color intensity produced is directly proportional to nitrite concentration, and nitrite concentration is directly related to nitrate concentration.

Zinc can alternatively be used as a sacrificial reducing agent, instead of Cd. Zn, however, is not as selective as the Cd. Zn tends to over-reduce the nitrate to NO, nitric oxide. Since NO doesn't react with sulphanilic acid in the diazotization reaction, it cannot participate in the Griess reaction and thus leads to erroneous test results. Additionally, the Zn surface is normally oxidized and requires an in-situ acid cleaning to activate it.

In the Griess reaction, nitrite ions present are reacted in an acidic medium with sulfanilic acid to form an intermediate diazonium salt. The diazonium salt couples with an azo dye agent like chromotropic acid to form a colored product. Chromotropic acid produces a pink color upon coupling with the diazo salt. Color intensity of the compound is directly proportional to the nitrite concentration of the water sample. The measurement wavelength is 507 nm for spectrophotometers or 520 nm for colorimeters. The nitrite concentration is then directly related to nitrate concentration. Genistic acid may, for example, be alternatively used as the azo dye agent. It produces an amber color upon coupling with the di-azo salt. Other azo dye agents can be used. For example, if N-alpha-naphthyl-ethylenediamine is used as the azo dye agent, a pink color develops upon coupling with the di-azo salt.

Novel water-soluble thioether compounds including an attached chromophore group have been synthesized. In the presence of nitrate and a water-soluble catalyst, the water-soluble chromophoric complexes undergo sulfoxidation with a concurrent color change. The color change is correlated to nitrate concentration. Further, depending on the extinction coefficient of the particular chromophore species attached, different measurement ranges are provided. Using this chemistry, novel methods, systems and kits for determining aqueous nitrate concentration may be provided in which all components (e.g., reagents and catalysts) are water soluble.

Figure 3:
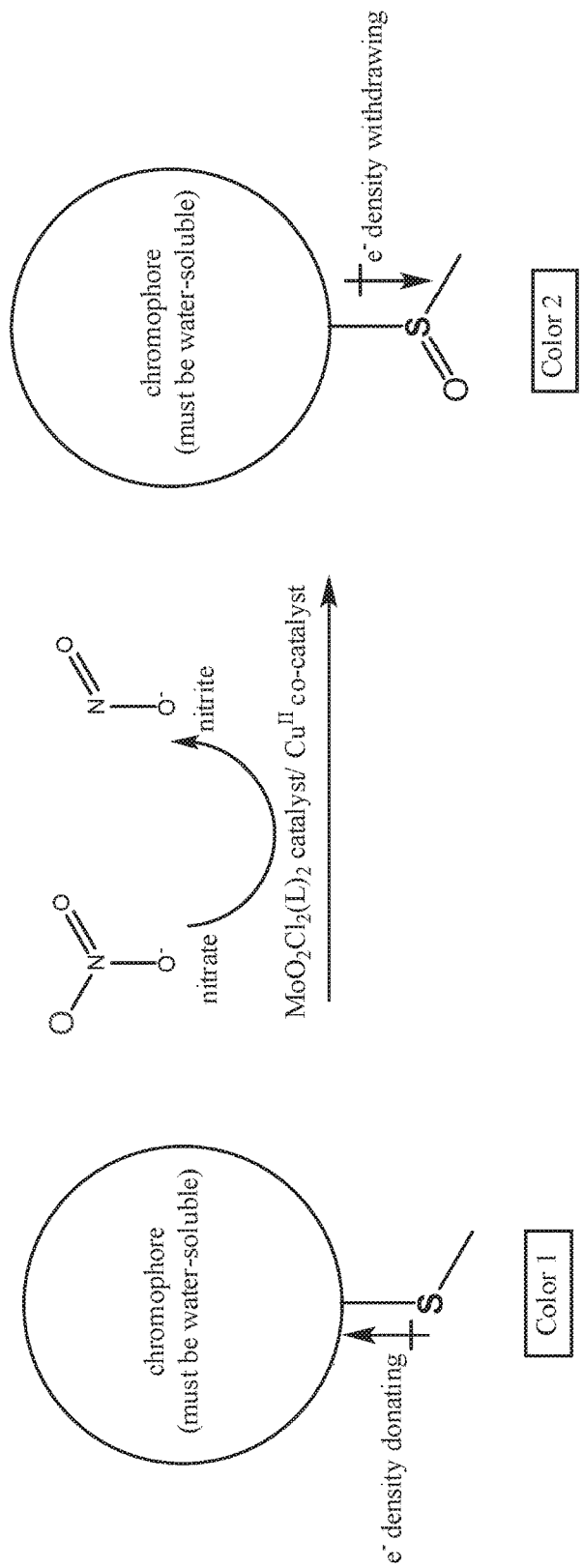
FIG. 3 illustrates the reduction of nitrate and concurrent sulfoxidation of a water soluble chromophore-thioether compound in the presence of a water soluble Mo catalyst/Cu(II) cocatalyst.

In a number of embodiments, aqueous nitrate is reduced to nitrite with concurrent sulfoxidation of a water soluble chromophore-thioether compound in the presence of a water-soluble catalyst system. The sulfoxidation causes a color change in the chromophore, as a result of a change in direction of electronic pull to/from the chromophore. The color change may be measured and correlated to nitrate concentration. FIG. 3 shows the reduction of nitrate and concurrent sulfoxidation of a water-soluble chromophore-thioether compound in the presence of a water-soluble Mo catalyst/Cu(II) cocatalyst system.

A general formula for a water-soluble chromophore-thioether compound hereof is $R^3$—S—$R^2$, wherein $R^3$ is a water soluble chromophore group and $R^2$ is an alkyl or hydrophilic group. $R^2$ may, for example, be a $C_1$ to $C_6$ alkyl group or a polyalkyleneoxide. The polyalkyleneoxide may, for example, include 4 to 5000 carbon atoms, 4 to 1000 carbon atoms or 20 to 1000 carbon atoms. The polyalkyleneoxide may for example, be polyethylene glycol.

$R^3$ is a hydrophilic conjugated chromophore group. A conjugated group refers to a group having connected p-orbitals with delocalized electrons in molecules with alternating single and multiple bonds. The conjugated group may be cyclic, acyclic, linear or mixed. The hydrophilic conjugated chromophore group may be a residue (or a derivative thereof) of a water-soluble, conjugated chromophore used in the reaction sequence forming the chromophore-thioether compound. In a number of embodiments, the hydrophilic chromophore group is selected from the group of a hydrophilic diarylmethane chromophore group, a hydrophilic triarylmethane chromophore group, a hydrophilic xanthene chromophore group, a hydrophilic boron-dipyrromethene (BODIPY) chromophore and/or and a hydrophilic pyrene chromophore group.

To improve water solubility, $R^3$ and/or $R^2$ may incorporate hydrophilic substituent species. Embodiments of hydrophilic groups incorporated on aromatic rings and/or other conjugated system include, but are not limited to, nitrogen-containing and/or oxygen-containing groups. In addition, charged species can also be incorporated to increase/improve hydrophilicity. For example, in a number of embodiments, one or more of a charged sulfonate group may be included as upon a substituent. Such substituents may, for example, be made by reacting attached nitrogen-containing groups, oxygen-containing groups and/or other groups with sultones (that is, cyclic sulfonic esters) that ring open to form sulfonates, thereby resulting in even greater hydrophilicity/water solubility.

To improve reactivity/reaction kinetics of the chromophore-thioether compound with nitrate, the chromophore group may, for example, include electron density donating moieties that result in increased electron density at the sulfur atom. For example, rate of reaction of an arylthioether with nitrate is dependent on the electron density of the aromatic ring(s). The higher the electron density on the ring, the faster the reaction rate and the higher the yield. As set forth above, high electron density on an aryl ring creates higher electron density on the sulfur atom. The sulfur becomes more electron rich when electron density in the aromatic ring increases via electron induction or resonance. The more electron rich the sulfur is, the more likely it is to participate in oxidization reactions and oxygen transfer. The more electron rich the sulfur is, the better it is as a reductant.

Figure 4:
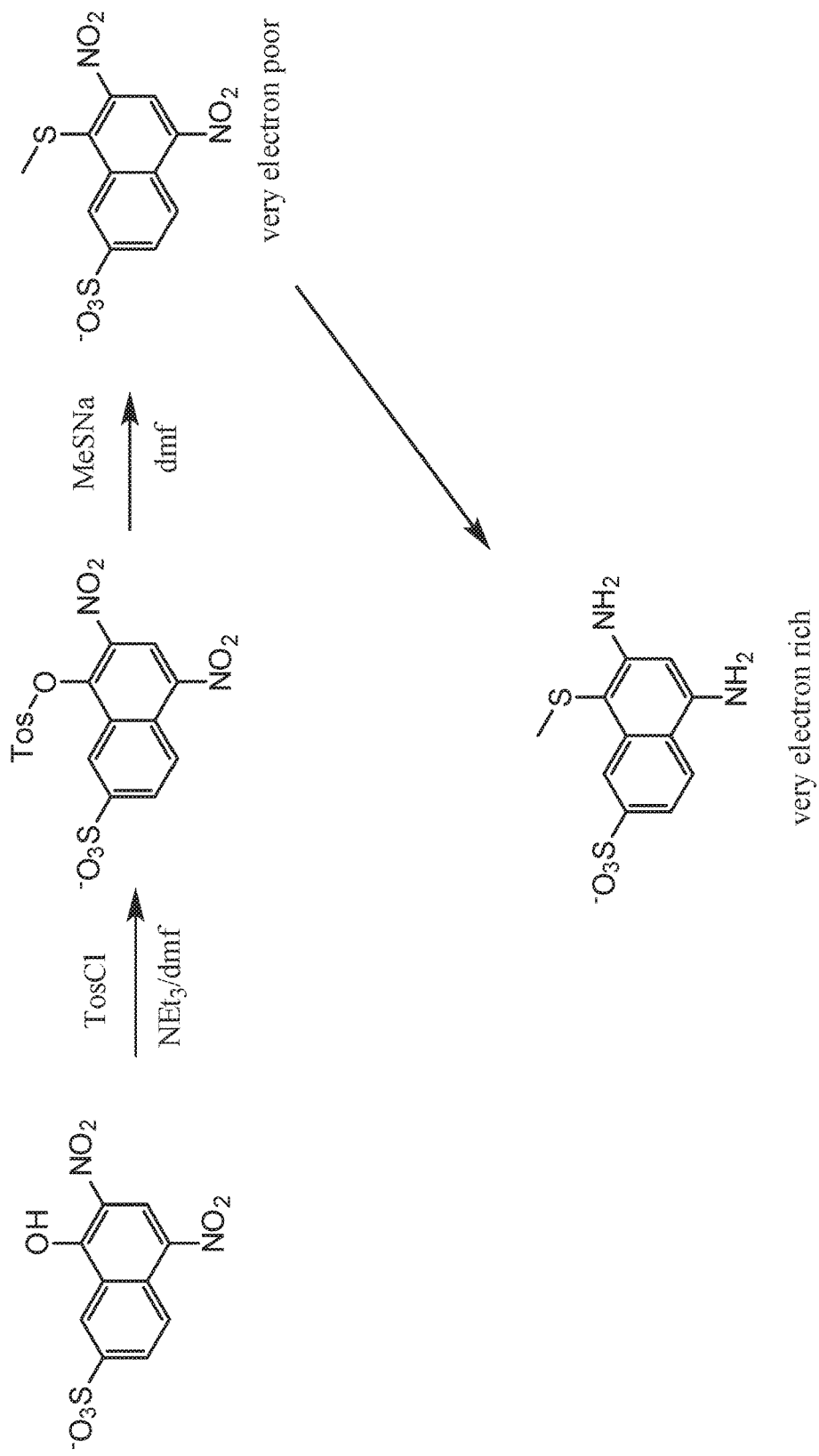
FIG. 4 illustrates an embodiment of a synthetic scheme for preparation of an embodiment of chromophore-thioether compound wherein the chromophore group is based on naphthol yellow.

FIG. 4 illustrates an embodiment of a reaction scheme for formation of a chromophore-thioether compound. The reaction scheme includes attaching a sulfur atom to naphthol yellow to create thiomethylether including a chromophore group which is a residue of naphthol yellow, retaining chromophoric functionality. Formation of a thiomethyl ether of FIG. 4 may, for example, occur in two steps. The reaction causes a color change. If one further converts the nitro functionality to amine functionality, it results in higher electron density on the ring (via electron induction and resonance) and higher electron density on the sulfur atom (see Target 1 of FIG. 4). This leads to higher reactivity of the thioether for sulfoxidation.

Figure 5:
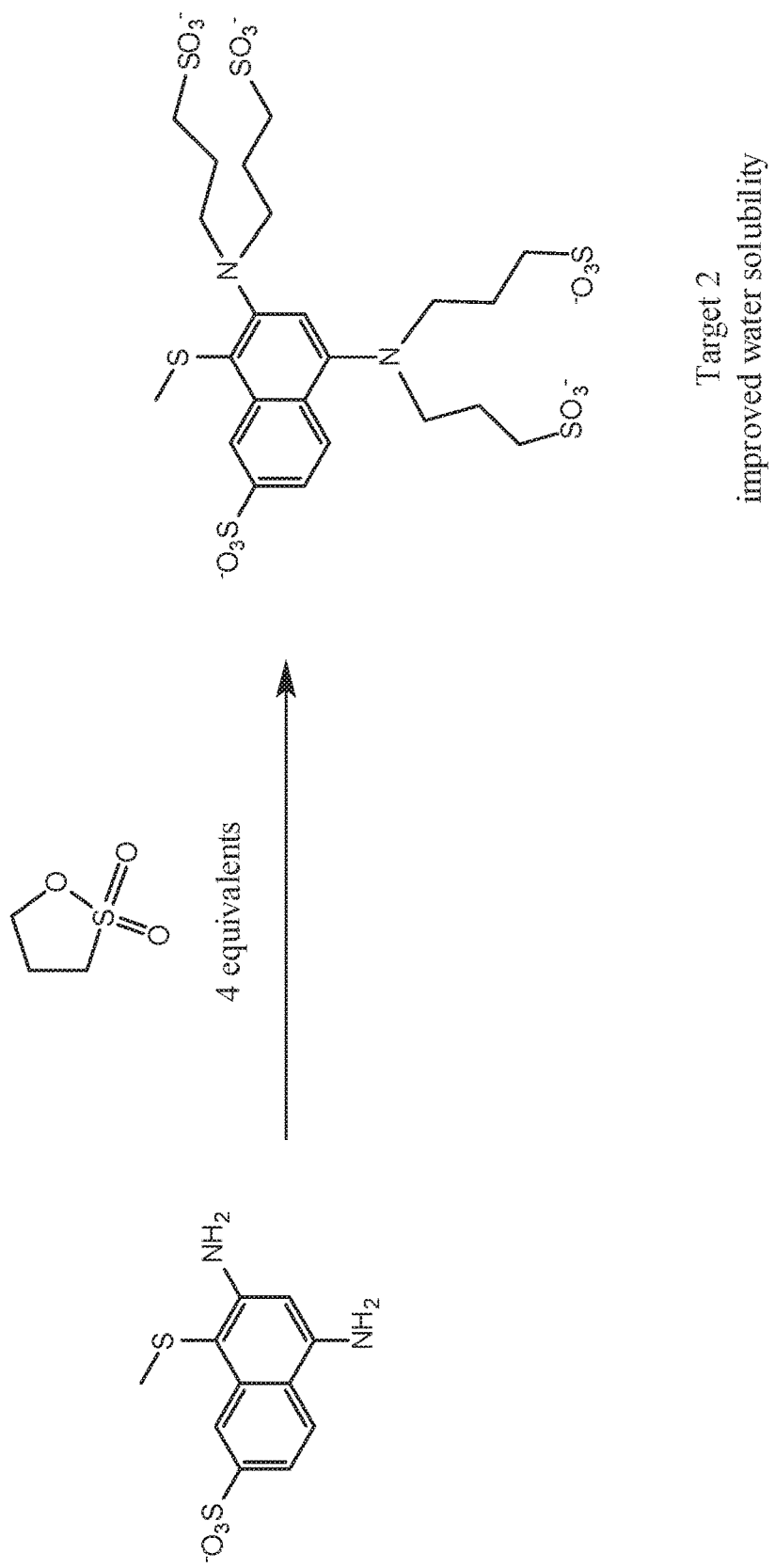
FIG. 5 illustrates preparation of a sulfonated chromophore-thioether compound from the chromophore-thioether compound of FIG. 4 for improved water solubility.

The chromophore-thioether compound of FIG. 4 may, for example, be further reacted with sultones to incorporate charged sulfonates as illustrated in FIG. 5. The amine functionality reacts with sultones (that is, cyclic sulfonic esters) that ring open to form charged sulfonates, thus resulting in the compound labeled Target 2 in FIG. 5 which has greater hydrophilicity/water solubility than Target 1 of FIG. 4. Reaction temperatures to prepare the chromophore-thioether compounds hereof may, for example, be at room temperature or below Depending on the extinction coefficient of the chromophore-thioether complex, different color changes upon sulfoxidation are realized. By tailoring the extent of color change, one can tailor the nitrate test sensitivity.

Selectivity of the sulfoxidation is improved using a water soluble Mo catalyst. It is desired to transfer only one oxygen atom to the thioether functionality. This may, for example, be achieved using the water-soluble Mo catalyst hereof. Stronger oxidants, like bleach or hydrogen peroxide, can transfer two oxygen atoms to the thioether functionality, resulting in unpredictable color change.

Figure 6A:
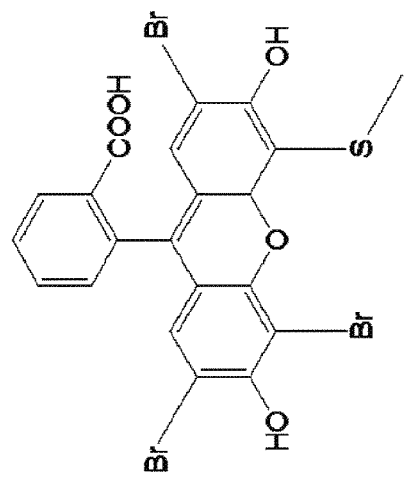
FIG. 6A illustrates a representative example of a synthetic scheme for synthesis of a thioether based upon an eosin Y diacetate chromophore.
Figure 6A:
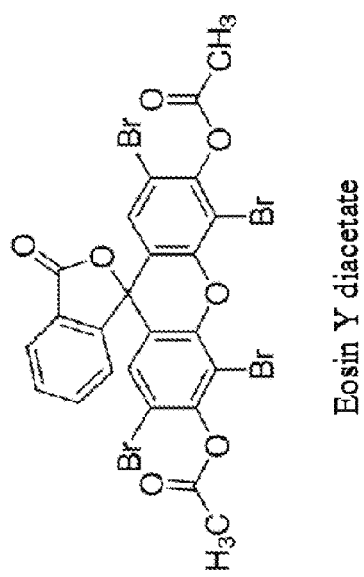
Figure 6B:
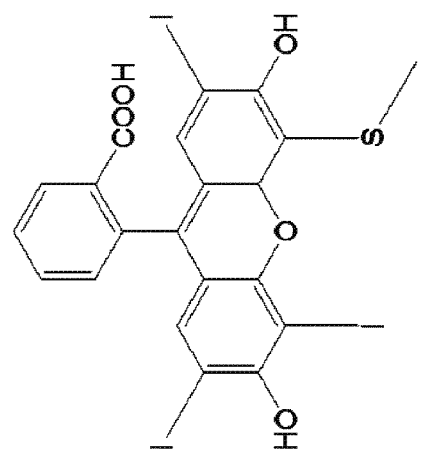
FIG. 6B illustrates a representative example of a synthetic scheme for synthesis of a thioether based upon the erythrosine B chromophore.
Figure 6B:
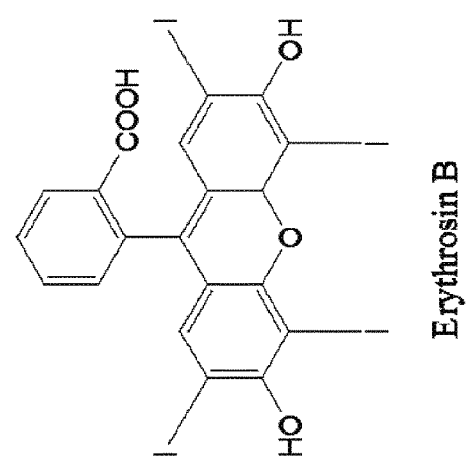
Figure 6C:
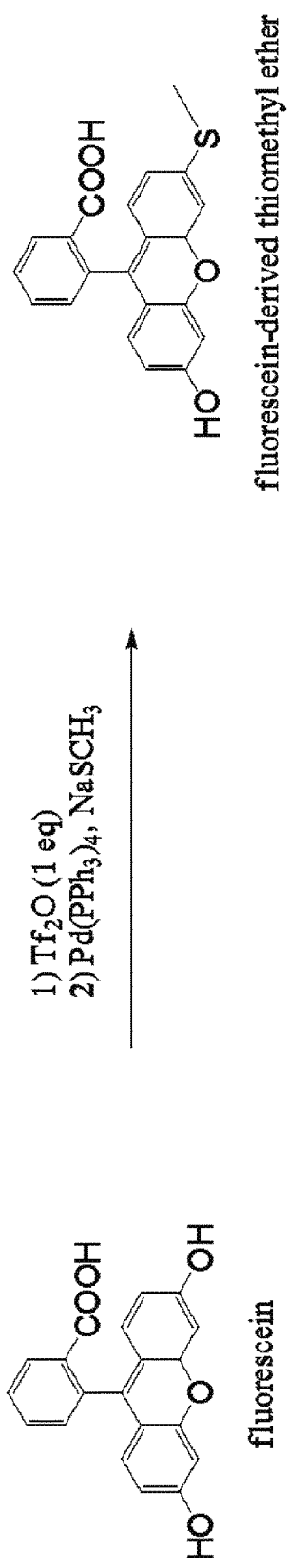
FIG. 6C illustrates a representative example of a synthetic scheme for synthesis of a thioether based upon a fluorescein chromophore.
Figure 6D:
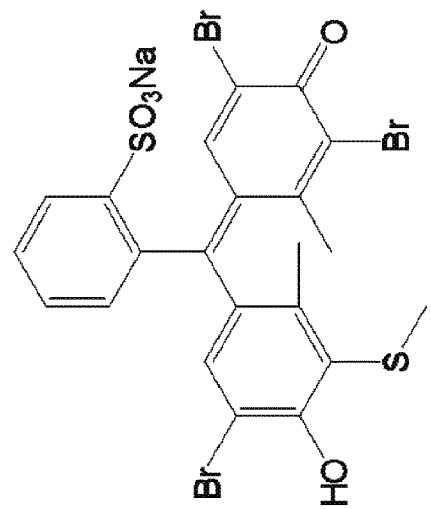
FIG. 6D illustrates a representative example of a synthetic scheme for synthesis of a thioether based upon a triphenylmethane chromophore.
Figure 6D:
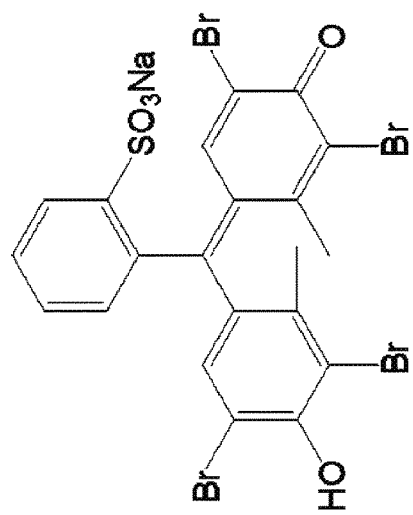
Figure 6E:
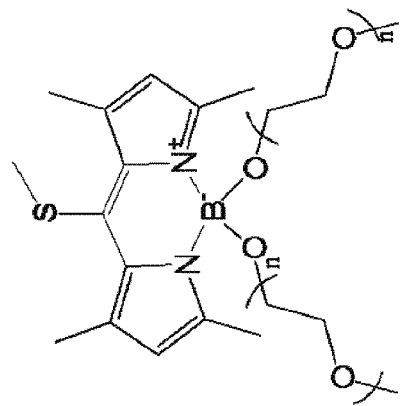
FIG. 6E illustrates a representative example of a synthetic scheme for synthesis of a thioether based upon a boron-dipyrromethene (BODIPY) chromophore.
Figure 6E:
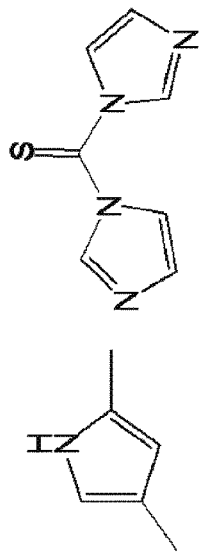
Figure 6F:
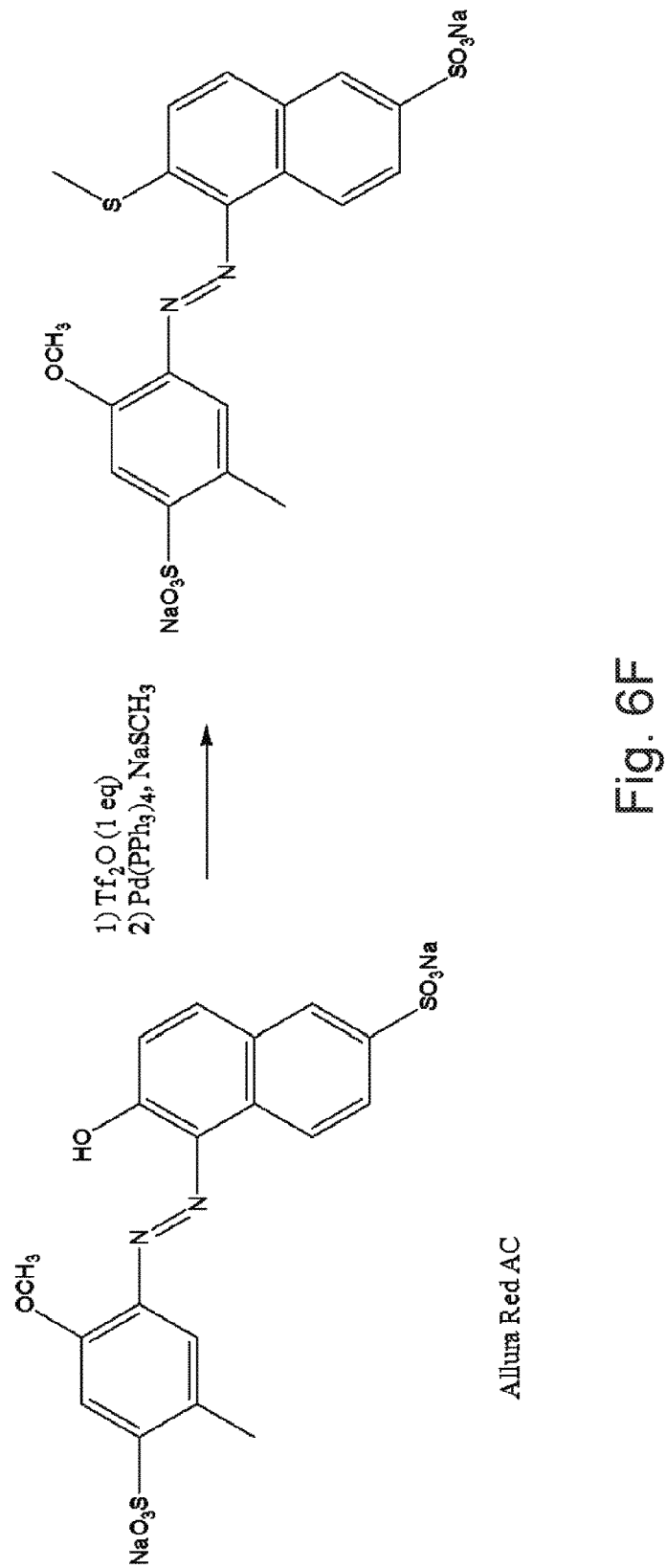
FIG. 6F illustrates a representative example of a synthetic scheme for synthesis of a thioether based upon a diazo chromophore.

FIGS. 6A through 6H illustrate embodiments of synthetic schemes for synthesis of additional chromophore-thioether compounds. FIGS. 6A through 6C illustrate the synthesis of fluorescein derived chromophore-thioether compounds. In that regard, FIG. 6A illustrates a representative example of a synthetic scheme for synthesis of a thioether based upon an eosin Y diacetate chromophore. FIG. 6B illustrates a representative example of a synthetic scheme for synthesis of a thioether based upon the erythrosine B chromophore. FIG. 6C illustrates a representative example of a synthetic scheme for synthesis of a thioether based upon a fluorescein chromophore. FIG. 6D illustrates a representative example of a synthetic scheme for synthesis of a thioether based upon a triphenylmethane chromophore. FIG. 6E illustrates a representative example of a synthetic scheme for synthesis of a thioether based upon a boron-dipyrromethene (BODIPY) chromophore. FIG. 6F illustrates a representative example of a synthetic scheme for synthesis of a thioether based upon a diazo chromophore. FIGS. 6G and 6H illustrate representative examples of a synthetic scheme for synthesis of thioethers based upon pyrene derived chromophores.

Water soluble catalysts were also synthesized. A molybdenum-based, water-soluble catalyst having the formula $MoO_2Cl_2(L)_2$ wherein L is a hydrophilic group was used in a number of embodiments. In several embodiments, L is a water soluble phosphine. For example, L can be trisulfonated-triphenylphosphineoxide which is commercially available, for example, from Strem Chemical, Inc. of Newburyport, Mass. A water-soluble Mo catalyst was, for example, synthesized by mixing an excess of trisulfonated-triphenylphosphineoxide with a $MoO_2Cl_2$ complex at room temperature.

In addition to the water-soluble Mo catalyst, a cocatalyst such as a water-soluble $Cu^{2+}$ cocatalyst can be used in the oxidation-reduction reaction. In a number of embodiments, the water-soluble $Cu^{2+}$ cocatalyst is $Cu(NO_3)_2$. Other water-soluble $Cu^{2+}$ cocatalysts include copperchloride ($CuCl_2$) and copper(II) sulfate ($Cu(SO_4)$).

The oxidation-reduction reaction, as shown in FIG. 3, proceeds directly with addition of the water-soluble Mo catalyst. Reaction rates are significantly faster when the $Cu^{2+}$ cocatalyst is also used.

To ensure complete reduction of nitrate, the molar amount of the chromophore-thioether compound may, for example, be about a factor of 5-100 greater than the analyte (nitrate), which is generally present at a maximum of about 15 ppmw. The homogeneous Mo catalyst may, for example, be used at about a 1:10 molar ratio compared to the chromophore-thioether compound.

Systems or kits for determining nitrate concentration based on the above methodologies may be prepared. The kit may, for example, include an analysis system comprising a water-soluble chromophore-thioether compound chosen to reduce nitrate in the aqueous sample to nitrite, a water-soluble catalyst, a system to measure a color change, and a system to correlate the color change to nitrate concentration.

The water soluble chromophore-thioether compounds and water-soluble catalyst used in the kit are described above. The system to measure color generation can be a spectrometer, colorimeter, photometric device, color disc, color block, or the like. The system to correlate color generation to nitrate concentration may, for example, include a look-up table, color comparator, a processor system (for example, including a microcomputer or other computer), and/or the like.

Figure 7:
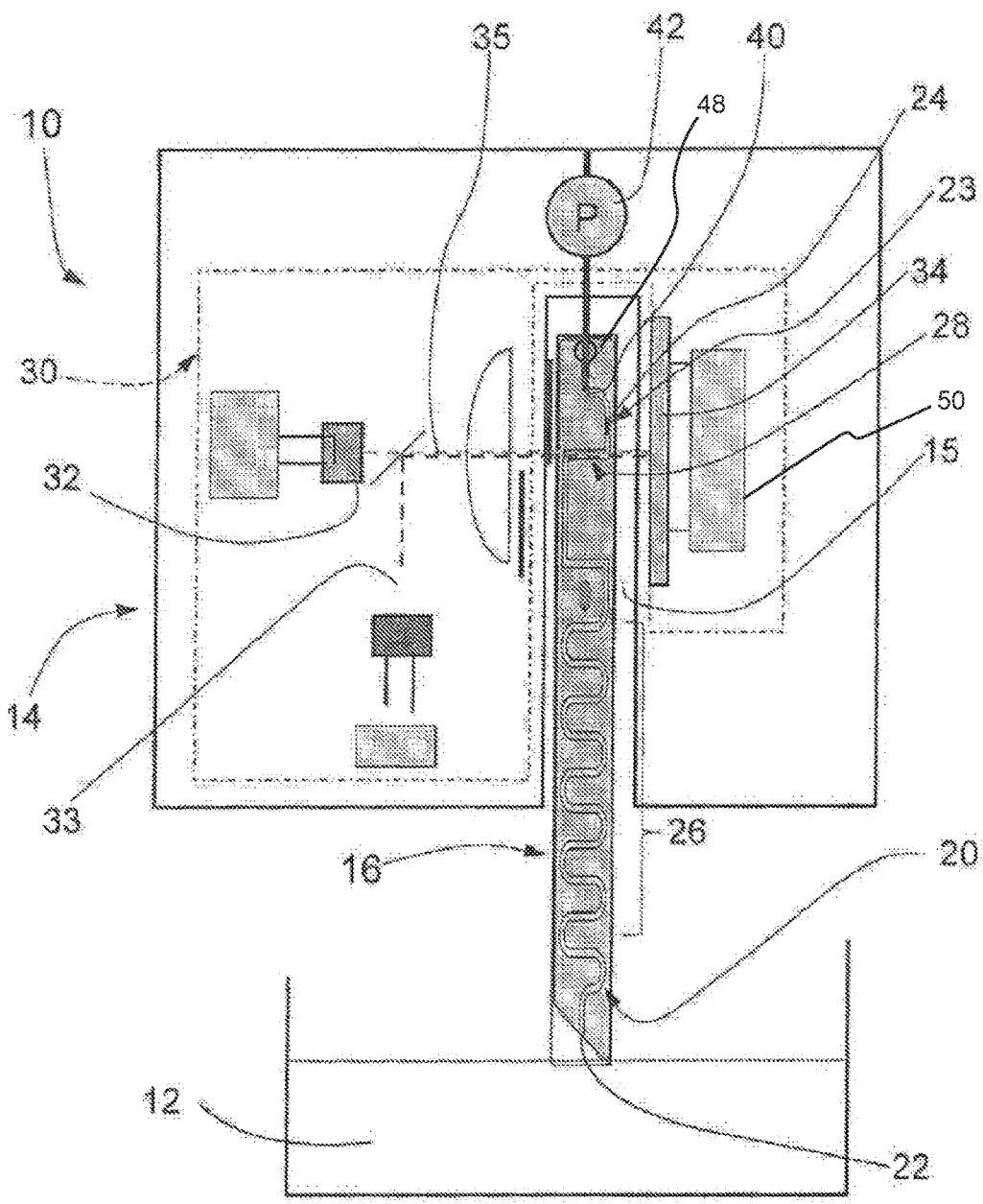
FIG. 7 illustrates an embodiment of a system of kit hereof including a portable analyzer and a test element.

In several embodiments of a kit to determine nitrate concentration, a mobile or portable instrument is used. An example of a portable instrument suitable for user in the kits hereof is set forth in U.S. Pat. No. 9,052,302, the disclosure of which is incorporated herein by reference. FIG. 7 schematically illustrates a mobile water-analyzing system 10 for a quantitative determination of a nitrate analyte in, for example, a water-sample. System 10 includes a basic unit 14 and a removable disposable test element 16 which is illustrated inserted into basic unit 14. Test element 16 is provided with a test-element body 18 made, for example, of a polymeric material. Test-element body 18 is provided with a sample-line 20 which may, for example, be formed as a groove. The side of the groove opening of test-element body 18 may be closed with a cover (for example, a plastic film or an aluminum cover, which is not shown).

Sample-line 20 is provided with an inlet opening 22 which is positioned at the distal end, referring to basic unit 14, and through which a water-sample is sucked from a water-reservoir 12. Adjacent to and, in the flow direction, behind inlet opening 22. is a meander-like mix section 26 of the sample-line 20 in which a reagent system as described herein and the drawn water-sample are homogeneously mixed.

A measuring section 28 is arranged adjacent to mix section 26 in which a quantitative determination may be performed. In a number of embodiments, measuring section 28 is a photometrical section, whereby measuring section 28 forms a measuring track for the respective photometrical/colorimetrical analyzer 30 of basic unit 14. Both sides of photometer/colorimeter section 28 may, for example, include a clear-transparent photometrical window 44, 46. Test-element body 18 may, for example, be fabricated from a clear transparent plastic which allows a measuring beam 35 to pass through measuring section 28.

Proximal to the measuring section 28 (that is, behind measuring section 28 as seen from inlet opening 22), is a reagent section 23 with a dry reagent system 24 as described herein. At the sample-line end opposite to the inlet opening 22 (that is, behind the first reagent section 23), a pump opening 40 as a pump element is provided which is connected with a pump actuator of sample pump 42 of basic unit 14 when test element 16 is inserted into basic unit 14.

Basic unit 14 is provided with an analyzer 30 which may, for example, include a photometer/colorimeter with one or more light source (two light sources 32, 33 are provided in the illustrate embodiment) and a detector 34 in operative connection with a processing system/controller 50. Light-sources 32, 33 may, for example, emit light of different wavelengths.

Test element 16 is provided with a positioning element 48 such as an opening. Positioning element/opening 48 cooperates with a respective snap element of the basic unit 14 so that test element 16 is fixed reproducibly and accurately. Test element receptacle of basic unit 14 may, for example, be formed as a slot 15 in which the test element 16 fits without any clearance.

The water-soluble chromophore-thioether reagents and catalyst hereof (collectively, a reagent system or analysis system) may, for example, be deposited on a test element such as test element 18, dried, and stored for later use. The test elements are insertable into a portable analysis system (as, for example, described above) to measure and correlate the color generation as described above. Multiple test elements hereof may be provided in a kit.

To reliably deposit reagents/catalysts on the test element, all components are preferably water-soluble and are preferably in a homogeneous solution. The solutions are preferably homogeneous with no deposition on the walls and no crystallization. In general, to achieve a homogeneous solution each of the components should not be too close to the solubility limit therefor, and the components should dissolve readily in water. In some embodiments, the reagents/catalyst are deposited in 4-6 microliters of water and dried in an nitrogen filled oven.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of measuring nitrate concentration in an aqueous sample, comprising:
   a. mixing the aqueous sample with a water-soluble thioether compound including a chromophore group in the presence of a water soluble catalyst, wherein the water-soluble thioether compound comprises a polyalkyleneoxide group, wherein the chomophore group is selected from the group consisting of a hydrophilic diarylmethane chromophore, a hydrophilic triarylmethane chromophore, a hydrophilic xanthene chromophore, a hydrophilic boron-dipyrromethene chromophore and a hydrophilic pyrene chromophore,
   b. measuring a color change, wherein the color change is responsive to a nitrite concentration within the aqueous sample, and
   c. correlating the color change to nitrate concentration, the correlating comprising correlating the nitrite concentration measured via the color change to a nitrate concentration.

2. The method of claim 1 wherein the water-soluble thioether compound is chosen to oxidize in the presence of nitrate.

3. The method of claim 2 wherein the water-soluble thioether compound has the formula:

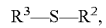

wherein $R^3$ is a hydrophilic chromophore group and $R^2$ is the polyalkyleneoxide group.

4. The method of claim 3 wherein the hydrophilic chromophore group comprises a residue of a water-soluble conjugated chromophore.

5. The method of claim 3 wherein the hydrophilic chromophore group comprises a residue of a water-soluble, substituted aromatic chromophore.

6. The method of claim 3 wherein the polyalkyleneoxide comprises 4 to 5000 carbon atoms.

7. The method of claim 1 wherein the water soluble catalyst comprises $MoO_2Cl_2(L)_2$ wherein L is a hydrophilic group.

8. The method of claim 7 wherein L comprises a water soluble phosphine.

9. The method of claim 8 wherein L is trisulfonated-triphenylphosphineoxide.

10. The method of claim 7 wherein the water soluble catalyst further comprises a $Cu^{2+}$ co-catalyst.

11. The method of claim 1 wherein the color change occurs in the visible light spectrum.

12. The method of claim 11 wherein the color change occurs between a wavelength of 500 nm and 700 nm.

13. The method of claim 1 wherein the measuring of the color change is measured using a device selected from the group consisting of spectrometer, colorimeter, photometric device, color disc, and color block.

14. The method of claim 1 wherein a detection range of nitrate is between about 0 ppmw and 15 ppmw.

* * * * *